(12) United States Patent
Fan

(10) Patent No.: US 10,512,450 B2
(45) Date of Patent: Dec. 24, 2019

(54) SHEAR WAVE ESTIMATION FROM ANALYTIC DATA

(71) Applicant: Liexiang Fan, Sammamish, WA (US)

(72) Inventor: Liexiang Fan, Sammamish, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1644 days.

(21) Appl. No.: 14/035,860

(22) Filed: Sep. 24, 2013

(65) Prior Publication Data

US 2015/0087976 A1    Mar. 26, 2015

(51) Int. Cl.
| | | |
|---|---|---|
| *A61B 8/08* | (2006.01) | |
| *G01S 7/52* | (2006.01) | |
| *G01S 15/89* | (2006.01) | |

(52) U.S. Cl.
CPC ............ *A61B 8/485* (2013.01); *A61B 8/5207* (2013.01); *G01S 7/52022* (2013.01); *G01S 7/52042* (2013.01); *G01S 7/52071* (2013.01); *G01S 7/52073* (2013.01); *G01S 15/8915* (2013.01); *A61B 8/5223* (2013.01); *G01S 15/8979* (2013.01); *G01S 15/8993* (2013.01)

(58) Field of Classification Search
CPC combination set(s) only.
See application file for complete search history.

(56) References Cited

U.S. PATENT DOCUMENTS

| | | | |
|---|---|---|---|
| 5,606,971 A * | 3/1997 | Sarvazyan | 600/438 |
| 7,252,004 B2 | 8/2007 | Fink et al. | |
| 2004/0167403 A1 * | 8/2004 | Nightingale | A61B 5/0053 600/437 |
| 2005/0004463 A1 | 1/2005 | Chen et al. | |
| 2006/0052699 A1 * | 3/2006 | Angelsen | A61B 8/14 600/437 |
| 2008/0249408 A1 | 10/2008 | Palmeri et al. | |
| 2009/0124901 A1 | 5/2009 | Fink et al. | |
| 2010/0016718 A1 | 1/2010 | Fan | |
| 2012/0089019 A1 | 4/2012 | Fan | |
| 2012/0215101 A1 * | 8/2012 | Maleke et al. | 600/438 |

OTHER PUBLICATIONS

Henni et al., "Shear wave induced resonance elastography of soft heterogeneous media", Journal of Biomechanics 43 (2010) pp. 1488-1493. (Year: 2010).*
Eskandari et al., "Bandpass Sampling of High-Frequency Tissue Motion", IEEE Transactions on Ultrasonics, Ferroelectrics, and Frequency Control, vol. 58, No. 7, Jul. 2011. pp. 1332-1343. (Year: 2011).*
Hoyt et al., "Two-Dimensional Sonoelastographic Shear Velocity Imaging", Ultrasound in Med. & Biol., vol. 34, No. 2, pp. 276-288, 2008 (Year: 2008).*

(Continued)

*Primary Examiner* — James M Kish

(57) ABSTRACT

Shear wave characteristics are estimated from analytic data. Measures of displacement are converted into complex representations. The magnitude and/or phase components of the complex representation may be used for estimating various characteristics, such as velocity, center frequency, attenuation, shear modulus, or shear viscosity. The zero-phase of the phase component represents an occurrence of the shear wave at that location.

14 Claims, 3 Drawing Sheets

(56) References Cited

OTHER PUBLICATIONS

Yang Shen et al., "Precise tracking of impulsive acoustic radiation force induced small displacements for shear wave speed estimation", Ultrasonics Symposium, 2011 IEEE International, Oct. 18, 2011, pp. 2402-2407.
Deffieux, T. et al., "Shear Wave Spectroscopy for In Vivo Quantification of Human Soft Tissues Visco-Elasticity", IEEE Transactions on Medical Imaging, IEEE Service Center, Piscataway, NJ, US, vol. 28, No. 3, Mar. 1, 2009, pp. 313-322.
M. L. Palmeri et al., "Acoustic radiation force-based elasticity imaging methods", Ultrasound in Medicine & Biology, vol. 35, No. 11, Jun. 8, 2011, pp. 1-12.
EP Search Report dated Jun. 17, 2015 from counterpart EP application No. 14183645.2, 10 pages.

\* cited by examiner

SHEAR WAVE ESTIMATION FROM ANALYTIC DATA

BACKGROUND

The present embodiments relate to ultrasound imaging. In particular, imaging based on detection of shear waves is provided.

Current time-of-flight estimation of the shear wave propagation either tracks some attribute of the waveform, such as the peak displacement, or computes the delay lag of the waveforms. The former uses only a single data point, so is error prone. The later is limited by sampling resolution and suffers from a lack of accuracy.

BRIEF SUMMARY

By way of introduction, the preferred embodiments described below include methods, instructions, and systems for shear wave estimation from analytic data. Measures of displacement are converted into complex representations. Magnitude and/or phase components of the complex representations may be used for estimating various characteristics, such as velocity, center frequency, attenuation, shear modulus, or viscosity. The zero-phase of the phase component represents an occurrence of the shear wave at that location.

In a first aspect, a method is provided for shear wave estimation from analytic data. An acoustic radiation force excitation is transmitted into a patient. Displacements at locations of tissue within a patient are measured with ultrasound in response to a shear wave resulting from the acoustic radiation force excitation. A processor constructs analytic data from the displacements. A characteristic of the shear wave is estimated from the analytic data. An image that is a function of the characteristic is displayed.

In a second aspect, a non-transitory computer readable storage medium has stored therein data representing instructions executable by a programmed processor for shear wave estimation from analytic data. The storage medium includes instructions for measuring, with ultrasound, real displacement data at locations of tissue within a patient in response to a shear wave resulting from an acoustic radiation force excitation, constructing analytic displacement data from the real displacement data, computing phases of the complex displacement data for each of the locations, estimating a shear wave velocity from zero crossings of the phases, and generating an image indicating the shear wave velocity.

In a third aspect, a non-transitory computer readable storage medium has stored therein data representing instructions executable by a programmed processor for shear wave estimation from analytic data. The storage medium includes instructions for measuring, with ultrasound, real displacement data at locations of tissue within a patient in response to a shear wave resulting from an acoustic radiation force excitation, constructing analytic displacement data from the real displacement data, filtering the analytic displacement data at different frequencies, calculating shear velocities as a function of the frequencies, and estimating shear modulus, viscosity, or shear modulus and viscosity from the shear velocities as a function of the frequencies.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Analytical data (complex format) of the displacement profile is constructed. Multiple data points in the phase curve fitting may be used. By finding zeros values of the phase curve, there are no resolution limits. Various characteristics may be estimated from the analytic data. For example, the zero-crossing times of the phases for different locations are calculated. These times as a function of location may be fit to a monotonic function (e.g., a line) with multiple points. The times may be used to estimate velocity.

In one embodiment, the analytical displacement data is constructed from the estimated real displacement data. The phase and magnitude of the analytical displacement data is computed. The phase of the complex displacement data is estimated, and the zero-crossing of the phase information is found by fitting the phase into a monotonic function. Group velocity, and/or attenuation may be estimated from the zero-crossing information. The center frequency can be estimated from the slope of the phase versus time. A line may be fit to find the slope.

In another embodiment, a filter bank is applied to the analytic displacement data. Shear velocity is estimated from the analytic displacement data for each of the multiple narrow bands. The velocity as a function of frequency is used to estimate shear modulus and shear viscosity from a single acoustic radiation force impulse (ARFI) excitation.

The time delay estimation may be generalized. The separation of the displacement estimation and time delay estimation is performed in one embodiment. In other embodiments, these operations may be mixed in the computation step in certain way. In one embodiment, operations are applied to detection signals of at least two spatial locations to obtain the desired parameters, such as time delay. These operations include mutual, self, or mixing of the mutual and self information extraction, such auto- and cross-correlations.

Figure 1:
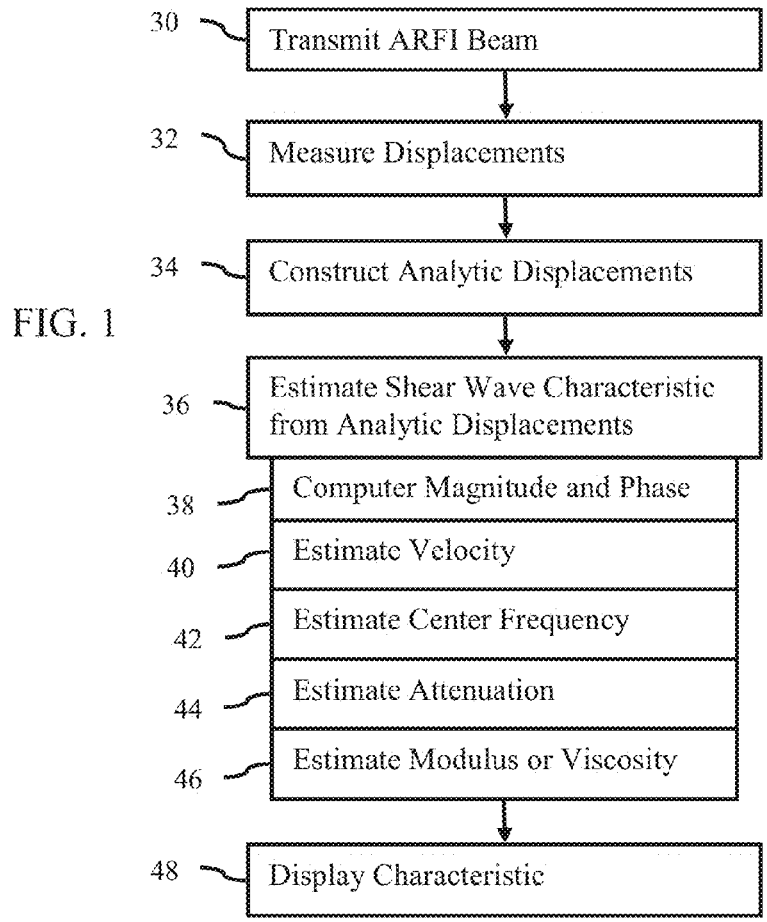
FIG. 1 is a flow chart diagram of one embodiment of a method for shear wave estimation from analytic data.

FIG. 1 shows a method for shear wave estimation from analytic data. The method is implemented by the system of FIG. 6 or a different system. Additional, different, or fewer acts may be provided. For example, any combination of one or more (e.g., fewer than all or all) of acts 40, 42, 44, and 46 are performed. As another example, act 48 is not performed. The estimated characteristic of the shear wave, tissue, or interaction of the shear wave with tissue is stored or transmitted rather than being displayed. The acts are performed in the order described or shown, but may be performed in other orders.

Figure 2:
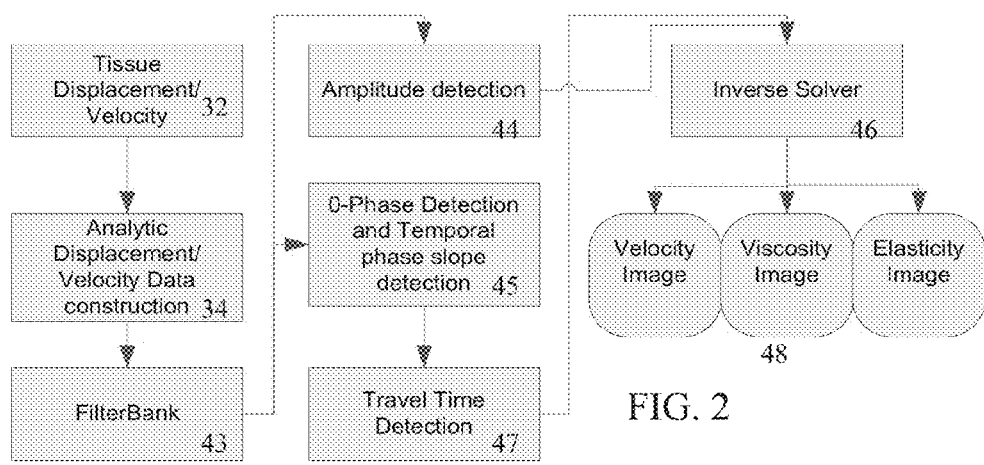
FIG. 2 is a flow chart diagram of another embodiment of a method for shear wave estimation from analytic data.

FIG. 2 shows another embodiment of a method for shear wave estimation from analytic data. The same acts are labeled with the same numbers. Acts 45 and 47 are performed for estimating the modulus or viscosity. Three different image options for the display of act 48 are shown, but only one, a combination of any two, or none are provided in other embodiments. Other combinations of acts using analytic data of the displacement profile for shear wave estimation may be provided.

In act 30, an acoustic excitation is transmitted into a patient. The acoustic excitation acts as an impulse excitation for causing displacement. For example, a 400 cycle transmit waveform with power or peak amplitude levels similar or lower than B-mode transmissions for imaging tissue is transmitted as an acoustic beam. In one embodiment, the transmission is a shear wave generating sequence applied to the field of view. Any acoustic radiation force impulse (ARFI) or shear wave imaging sequence may be used.

The transmission is configured by power, amplitude, timing, or other characteristic to cause stress on tissue sufficient to displace the tissue at one or more locations. For example, a transmit focus of the beam is positioned near a bottom, center of the field of view or region of interest (ROI) to cause displacement throughout the field of view. The transmission may be repeated for different sub-regions or ROIs.

The excitation is transmitted from an ultrasound transducer. The excitation is acoustic energy. The acoustic energy is focused, resulting in a three-dimensional beam profile. The excitation is focused using a phased array and/or mechanical focus. The excitation may be unfocused in one dimension, such as the elevation dimension. The excitation is transmitted into tissue of a patient.

The impulse excitation generates a shear wave at a spatial location. Where the excitation is sufficiently strong, a shear wave is generated. The shear wave propagates through tissue more slowly than the longitudinal wave propagates along the acoustic wave emission direction. This difference in timing is used to isolate the shear wave from a longitudinal wave, such as sampling at locations at certain times. The shear wave propagates various directions, including a direction perpendicular to the direction of the applied stress. The displacement of the shear waves is greater at locations closer to the location at which the shear wave is generated. As the shear wave travels longitudinally, the magnitude of the shear wave attenuates.

In act 32, a displacement response to the shear wave in the patient is detected. For example, the displacement profiles for two locations are demonstrated in FIG. 3. The excitation causes displacement of the tissue. A shear wave is generated and propagates from the focal region. As the shear wave travels through tissue, the tissue is displaced. Timing and/or lateral location are used to distinguish the shear wave from other generated waves. Longitudinal waves or other causes of displacement may be used instead of shear. The tissue is forced to move in the patient.

Figure 3:
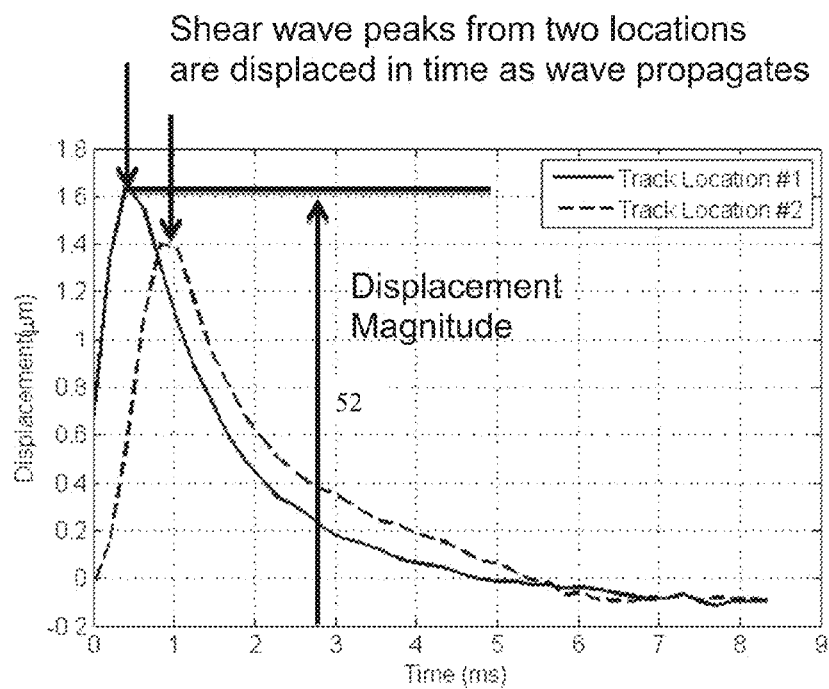
FIG. 3 is a graph showing two example displacement profiles as a function of time.

The displacement caused by the force or stress is measured. The displacement is measured over time at one or more locations. The displacement measurement may begin before the stress or impulse ends, such as using a different frequency or coding. Alternatively, the displacement measurement begins after the impulse ends. Since the shear, longitudinal or other wave causing the displacement in tissue spaced from the point or region of stress takes time to travel, the displacement from a relaxed or partially stressed state to a maximum displacement and then to a relaxed state may be measured, as represented in FIG. 3. A temporal profile of displacement is determined. Alternatively, the displacement is measured only while the tissue is relaxing from the maximum.

The measurement is of the amount of the displacement. The in-phase component of displacement can be measured using the ultrasound signal, so is not a complex representation. The tissue is moved in any direction. The measurement may be along the direction of greatest movement. The magnitude of the motion vector is determined. Alternatively, the measurement is along a given direction, such as perpendicular to the scan line regardless of whether the tissue is displaced more or less in other directions.

The displacement is detected with ultrasound scanning. Ultrasound data is obtained. At least some of the ultrasound data is responsive to the shear wave. A region, such as a region of interest, entire field of view, or sub-region of interest, is scanned with ultrasound. The region is monitored to detect the shear wave. The region is any size, such as 5 mm in lateral and 10 mm in axial. For example, B-mode scans are performed to detect tissue displacement caused by the shear wave. Doppler, color flow, or other ultrasound mode may be used to monitor for the shear wave.

For a given time, ultrasound is transmitted to the tissue or region of interest. Any now known or later developed displacement imaging may be used. For example, pulses with 1-5 cycle durations are used with an intensity of less than 720 mW/cm$^2$. Pulses with other intensities may be used. The monitoring is performed for any number of scan lines. For example, four or eight receive beams are formed in response to each transmission. After transmitting the excitation to generate the shear wave, B-mode transmissions are performed repetitively along a single transmit scan line and receptions along four or eight adjacent receive scan lines. In other embodiments, only a single receive beam or other numbers of receive beams are formed in response to each transmission. Additional transmit scan lines and corresponding receive line or lines may be used. Any number of repetitions may be used, such as about 120 times. Some of the ultrasound data, such as at the beginning or end of the repetitions, may not be responsive to the shear wave.

As the shear wave propagates through the scan lines, the B-mode intensity may vary due to displacement of the tissue. For the monitored scan lines, a sequence of data is provided representing a time profile of tissue motion resulting from the shear wave. Echoes or reflections from the transmission are received. The echoes are beamformed, and the beamformed data represents one or more locations. To detect the displacement, ultrasound energy is transmitted to the tissue undergoing displacement and reflections of the energy are received. Any transmission and reception sequence may be used.

By performing the transmitting and receiving multiple times, data representing a one, two, or three-dimensional region at different times is received. The transmission and reception are performed multiple times to determine change due to displacement. By repetitively scanning with ultrasound, the position of tissue at different times is determined.

The displacement is detected from the differences for each spatial location. For example, the velocity, variance, shift in intensity pattern (e.g., speckle tracking), or other information is detected from the received data as the displacement.

In one embodiment using B-mode data, the data from different scans is correlated as a function of time. For each depth or spatial location, a correlation over a plurality of depths or spatial locations (e.g., kernel of 64 depths with the center depth being the point for which the profile is calculated) is performed. For example, a current set of data is correlated multiple times with a reference set of data. The location of a sub-set of data centered at a given location in the reference set is identified in the current set. Different relative translations and/or rotations between the two data sets are performed.

The reference is a first set of data or data from another scan. The reference set is from before the ARFI pulse, but may be from after the ARFI pulse. The same reference is used for the entire displacement detection, or the reference data changes in an ongoing or moving window.

The correlation is one, two or three-dimensional. For example, correlation along a scan line away and toward the transducer or along a line perpendicular to the scan line is used. As another example, the translation is along two axes with or without rotation. In yet another example, the translation is along three axes with or without rotation about three or fewer axes. The level of similarity or correlation of the data at each of the different offset positions is calculated. The translation and/or rotation with a greatest correlation represents the motion vector or offset for the time associated with the current data being compared to the reference.

Any now known or later developed correlation may be used, such as cross-correlation, pattern matching, or minimum sum of absolute differences. Tissue structure and/or speckle are correlated. Using Doppler detection, a clutter filter passes information associated with moving tissue. The velocity of the tissue is derived from multiple echoes. The velocity is used to determine the displacement towards or away from the transducer. Alternatively, the relative or difference between velocities at different locations may indicate strain or displacement.

FIG. 3 shows two example displacement profiles of real displacements. The amplitude in distance of the motion vector over time from the reference data is shown. The period of analysis is over about 8 milliseconds, but may be longer or shorter (e.g., 12 milliseconds at a 4.8 kHz sample rate). Other displacement profiles are possible. Any number of locations may be measured for displacement, such as measuring every millimeter in the 10×5 mm region of interest. Displacement for each location and for each sample time is measured. This real displacement data represents a profile of amplitude as a function of time for each of a plurality of locations.

The displacements over time and/or space are used for calculation. In one embodiment, the displacements for different depths are combined, leaving displacements spaced in azimuth or along the propagation direction of the shear wave. For example, the displacements for a given scan line or lateral location are averaged over depth. Alternatively to averaging, a maximum or other selection criterion is used to determine the displacement for a given lateral location. Displacements for only one depth may be used. Displacements for different depths may be used independently.

In act 34, a processor constructs analytic data from the displacements. The real displacement data is converted into a complex representation. Since the displacements over time represent a profile having a curve or initially increasing followed by decreasing amplitude, the displacements may be converted into real and imaginary or in-phase and quadrature components. Other analytic data components may be used.

The analytic data is constructed by applying a Hilbert transform to the displacements as a function of time for each location. A Hilbert transform in the temporal domain converts the real displacement data into analytical displacement data. Other transforms than Hilbert may be used, such as filtering results of Fourier transforms.

For each location, a series of analytically represented measures of displacement result. The series is of the analytic displacements over time. Complex representations of the displacements of the displacement profile are provided for each location.

In act 36, a characteristic of the shear wave is estimated. The processor determines one or more values from the analytic data. The values are characteristics associated with the shear wave, such as characteristics of the shear wave itself, characteristics of the tissue, or characteristics of the shear wave interaction with the tissue. The characteristics of the shear wave are used for diagnosis. Any characteristic may be estimated, such as the velocity in act 40, the center frequency in act 42, the attenuation in act 44, the shear modulus in act 46, or the shear viscosity in act 46. One, combinations of multiple, additional, different, or fewer characteristics may be estimated.

A processor performs the calculation. The displacement information is used to determine the property without user input. Once the displacements are acquired, the processor automatically calculates the property for each location and/or time.

In act 38, the magnitudes and phases are computed from the analytic data. The complex representations of the displacements are used to find the magnitudes and phases. For each displacement (i.e., for each time at each location), the magnitude and phase of the displacement is determined. For example, the mag·cos(θ) representation is used where mag is the magnitude and θ is the phase.

Magnitude alone, phase alone, or both are computed. Different characteristics may be based on different aspects of the complex or analytic representation of the displacements.

Figure 4:
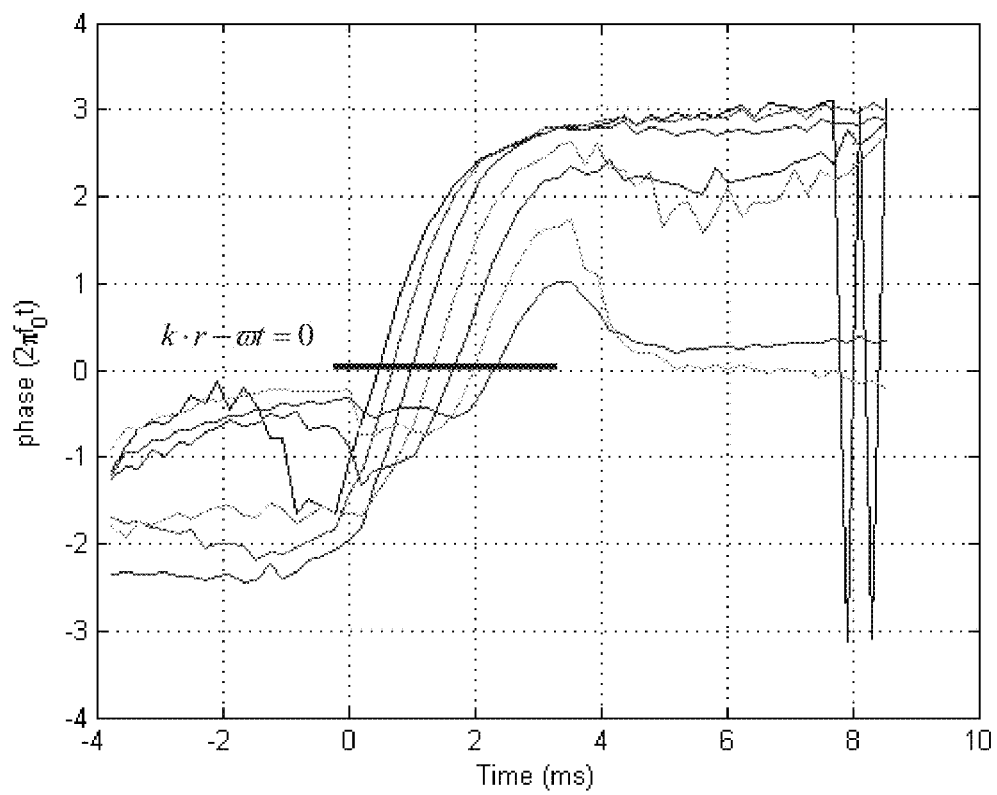
FIG. 4 is an example graph of phase as a function of time for different locations.

FIG. 4 shows the phase over time for each of seven locations. Time 0 corresponds to the creation of the shear wave. Each curve corresponds to the phase computed from the analytic displacement data for a given or specific spatial location. The zero phase point can be used to present the occurrence of the shear wave at that location, the curves are offset in time from each other in order of the spatial relationship of the locations.

In act 40, the velocity is estimated from the magnitude and/or phase. In one embodiment, the velocity is estimated from the magnitude information. The magnitude derived from the analytic data has a profile over time. The profile of this magnitude may be different than the profile of the measured or the in-phase component of displacement over time. The magnitude profile has a peak, which occurs at a given time. Other points in the profile may be used as an indication of the occurrence of the shear wave. Using the distance from the location to the origin of the shear wave and the difference in time from the generation of the shear wave and the occurrence of the peak, the velocity of the shear wave is determined. Correlation lag or other techniques may be used.

For a group velocity, the velocity based on displacements at different locations is used. A difference in time between two locations spaced from the origin of the shear wave is calculated. The distance between the two locations and the difference in time indicate the velocity between the two locations.

In another embodiment, the shear wave velocity is estimated from zero-crossings of the phases. The zero-crossings of the phase are identified. In FIG. 4, the zero crossings are highlighted by the horizontal line. The phase being equal to zero is represented by: $kr-\omega t=0$ where t is time, $\omega$ is angular frequency, k is wave number of shear wave and r is the propagation range.

Figure 5:
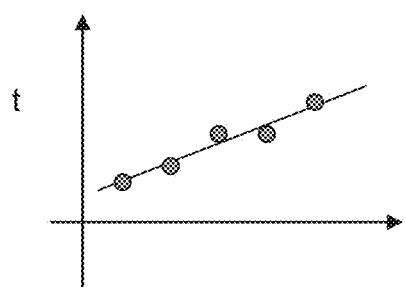
FIG. 5 is an example plot of time of zero-phase as a function of location.

The time of the zero crossing for each location is determined. The times may be used like the magnitude peaks. The time differences between locations and the distances between the locations are used to estimate the velocity. In another embodiment, a monotonic function is fit to a plot of the time as a function of location. The slope of the line indicates the group velocity. FIG. 5 represents this line fit to the zero-crossing times as a function of location for five locations.

In act 42, the center frequency of the shear wave is estimated from the analytic displacement data. Since different equipment or settings may result in different shear velocities for identical tissue, the center frequency may be used as a measure of similarity of the settings or equipment. The center frequency may be used to account for differences in velocity calculation at different times or between patients.

In one embodiment, the phase information is used. The slope of the phase profile at the zero-crossing indicates the center frequency. The slope of the phase as a function of time shows the frequency.

In another embodiment, the center frequency is calculated using a Fourier transform. A Fourier transform of the analytic displacement as a function of time is determined. From the resulting spectrum, a center frequency is calculated. Any measure of center frequency may be used. For example, the center frequency is the frequency corresponding to peak value of power spectrum.

The center frequencies from different locations may be averaged. An average or median center frequency may be calculated for a region of interest. Other combinations may be used.

In act 44, attenuation is estimated from the analytic displacement data. The magnitude from the analytic data is used to determine the attenuation.

The maximum magnitude of displacement over time for each location is found. The shear wave peak magnitudes at multiple locations along the propagation direction are calculated and used to derive the attenuation. Other measures of attenuation may be used.

The magnitude of displacement caused by the shear wave is determined. The magnitude may be derived from the displacement profile over time, such as identifying the maximum displacement. The magnitude of the maximum displacement is determined. The maximum displacement is calculated from the displacement profile. The peak or highest amount of motion or magnitude of shift by the tissue along a line, within a plane, or within a volume is calculated for the peak. The smoothed or filtered displacement curve is used for the maximum calculation. In other embodiments, the raw or unfiltered displacement curve may be used. The maximum value over the entire or portion of the profile is identified or determined. Alternatively, the magnitude may be from a given time based on a distance from the focal region to the monitored location.

The temporal profile for a given location indicates detection of the shear wave at that location. The profile is examined for a non-noise or single instance of variation. A peak in the profile, with or without temporal low pass filtering, indicates the passing of the shear wave front. The greatest displacement is selected, but the average, initial non-noise displacement, or other displacement statistic may be used to indicate the passing.

In other embodiments, the energy or power is calculated for each location and used to derive attenuation. The power of the displacement is the square of the magnitude. The energy of the displacement is the integral over time. The magnitude, energy and/or power of the displacement may be used.

The attenuation is given by the slope of the maximums over the locations. To calculate attenuation, ratios of adjacent maximum magnitudes are calculated. Alternatively, ratios of maximum magnitudes from non-adjacent (e.g., ratios from a reference to each of the locations) are calculated. The logs of the ratios provide the attenuations. An average attenuation over the azimuthally spaced locations may be used. Alternatively, the attenuation at each location is separately used. Other attenuation calculations may be used.

In an alternative embodiment, the attenuation is calculated for different frequencies. By filtering with narrow bands in act 43, the analytic displacement data for a given location is isolated for each of different frequencies. The attenuation as a function of frequency is determined.

In act 46, the shear modulus, viscosity, or shear modulus and viscosity are estimated. Other characteristics of the shear wave may be estimated.

In one embodiment, the attenuation or attenuation as a function of frequency is used to estimate the shear modulus or viscosity. FIG. 2 shows an example where amplitude (magnitude) is detected for different frequency bands in acts 43 and 44. The attenuation as a function of frequency is used for inverse solution in act 46 to provide viscosity or shear modulus.

In another embodiment, velocity as a function of frequency is used to estimate the shear modulus or viscosity. The dispersion of the shear wave is calculated from the analytical displacements. The dispersion is a measure of the velocity as a function of frequency. Any measure of dispersion may be used, such as a derivative of velocity as a function of frequency or slope of a line fit (e.g., linear regression fitting) to velocity as a function frequency.

In one embodiment, the analytic displacement data or magnitude and phase data is filtered as a function of time. The same data is filtered with different pass bands. For example, to obtain shear wave dispersion, a filter bank with ten or other number of center frequencies evenly distributed in a range, such as from 50 to 275 Hz, are applied to the shear wave analytic displacement data. The filters are temporal filters, so the process is repeated separately for each location. In this example, each filter has a 32 Hz bandwidth with increments of 11.25 Hz between 50 Hz to 275 Hz using a 2nd order Elliptic filter with 0.5 dB ripple and 40 dB stop band attenuation. Other filters may be used. The filters are implemented as discrete filters or by a processor.

The shear velocity for each center frequency or frequency band is calculated. For example, the maximum magnitude of the filtered analytic displacement data indicates passing of the shear wave. For the location, the time or duration for the shear wave to travel from the origin (e.g., transmit focal region) to the location is determined. The maximum displacement or other part of the displacement profile indicates the time of arrival of the shear wave. Using the timing from generation of the shear wave to arrival, the travel time is calculated. The time is known from the relative time between generation and detection of the shear wave. The travel time may be non-linear. The time and distance between locations may be used instead of or in addition to the time and distance from the creation.

The velocity of the shear wave is calculated from the timing information. The travel time is the inverse of the velocity. Using the distance and the travel time, the velocity is calculated. The distance is known from the scan line spacing (i.e., the transmit beam position for generating the shear wave and the receive beam position for detecting the shear wave).

Other techniques may be used to detect the peak in the profile and corresponding time and velocity. For example, a regression is applied. Since the shear wave velocity is linear, a robust linear regression with automated outlier detection may indicate the shear wave velocity. The ultrasound data for all of the sample points in the region of interest is plotted for distance as a function of time or by time and distance. The linear regression is applied to the plot or data, providing a line fit to the data. The slope of the line indicates the shear wave velocity.

In another embodiment, the zero-crossings of the phases are used instead of the magnitudes for calculating the velocity. The zero-phase for each frequency band is determined in act 45. The analytic data output by each filter is processed to determine phase as a function of time. The frequency is the filtering frequency or a frequency calculated from the slope of the phase.

The time of the zero-crossing indicates the occurrence of the shear wave at the location. In act 47, the time of the zero-crossing for each frequency is determined at each location. The difference in time and distance between locations is used to calculate the velocity. Since velocities are calculated for different frequencies for a given location, the velocity as a function of frequency is determined.

Since velocities are provided for different frequency bands, the dispersion of the shear velocity by frequency is provided. A derivative or other characteristic of this dispersion curve or line or the curve itself indicates the dispersion.

In act 46, the shear modulus, viscosity, or both are estimated. Other characteristics of the shear or tissue response to shear may be estimated.

The estimate is a function of the velocity as a function of frequency, attenuation, other information derived from the analytic data, or combinations thereof. In one embodiment, the velocities calculated for the different frequency pass bands of the analytic displacement at a given location over time are used.

Parametric curve fitting, inverse solutions, iterative solutions, or other approaches for determining the shear modulus and/or viscosity from values of other variables are used. For example, the shear modulus and viscosity are estimated though curve fitting to the relationship of velocity to frequency. The relationship may be expressed as:

$$c_t = \sqrt{\frac{2(\mu^2 + \omega^2 \eta^2)}{\rho(\mu + \sqrt{\mu^2 + \omega^2 \eta^2})}}$$

where $c_t$ is the velocity, $\mu$ is the shear modulus, $\omega$ is the angular frequency, and $\eta$ is the shear viscosity. The curve fitting solves for the shear modulus and viscosity given the velocities and frequencies. Other solutions or relationship functions may be used.

The estimation may be a calculated solution. Alternatively, a pattern of the input values or parameters derived from the input values are used as inputs to a table for outputting the modulus and/or viscosity based on an experimental or pre-calculated relationship.

The processor calculates a value for the characteristic for each location and/or for a region of interest. The estimation is repeated for the velocity as a function of frequency, attenuation, or other information from the analytic data of the different locations. The estimated characteristics are used separately or may be combined into fewer values than locations. Alternatively, the characteristics are calculated for one location, or the input values for multiple locations are used to estimate one value for each characteristic.

In act 48, an image of the estimated characteristic is generated. FIG. 2 shows images for the velocity, shear modulus, and shear viscosity as examples. Additional, different, or fewer characteristics may be estimated and displayed.

In one embodiment, an alphanumeric value representing the estimated characteristic is displayed on a screen. For example, a single shear modulus value is displayed in text. Alternatively or additionally, a graphic (e.g., curve or icon) representing the estimated characteristic over time or space is displayed. Reference to a scale or other reference may be displayed.

In other embodiments, the characteristic as a function of location is displayed in a two-dimensional representation. For example, shear wave imaging is performed. The shear wave velocity, modulus or other information determined from tissue reaction to a shear wave is displayed. Any shear imaging may be used. The displayed image represents shear wave information for the region of interest or the entire imaging region. For example, where shear velocity values are determined for all of the grid points in a region of interest or field of view, the pixels of the display represent the shear wave velocities for that region. The display grid may be different from the scan grid and/or grid for which displacements are calculated.

The shear wave information is used for a color overlay or other modulation of display values. Color, brightness, luminance, hue, or other display characteristic is modulated as a function of the shear wave characteristic, such as the shear wave velocity. The image represents a two- or three-dimensional region of locations. The shear data is in a display format or may be scan converted into a display format. The shear data is color or gray scale data, but may be data prior to mapping with gray scale or color scale. The information may be mapped linearly or non-linearly to the display values.

The image may include other data. For example, shear wave information is displayed over or with B-mode information. B-mode or other data representing tissue, fluid, or contrast agents in the same region may be included, such as displaying B-mode data for any locations with shear wave velocity below a threshold. The other data assists the user in determining the location of the shear information. In other embodiments, the shear wave characteristic is displayed as an image without other data.

Other characteristics may be displayed substantially simultaneously with the shear wave imaging. Substantially accounts for visual perception of the view. Displaying two images sequentially with sufficient frequency may allow the viewer to perceive the images as being displayed at a same time.

Any format for substantially simultaneous display may be used. In one example, the shear velocity or modulus image is a two-dimensional image. The shear viscosity and/or center frequency is text, a graph, two-dimensional image, or other indicator of the values. A cursor or other location selection may be positioned relative to the shear image. The cursor indicates selection of a location associated with shear wave velocity information. For example, the user selects a pixel associated with an interior region of a lesion, cyst, inclusion, or other structure. One or more other characteristics for the selected location are then displayed as a value, a pointer along a scale, or other indication.

In another embodiment, shear wave velocity and modulus or viscosity images are displayed substantially simultaneously. For example, a dual-screen display is used. The shear wave velocity image is displayed in one area of the screen. The modulus or viscosity as a function of location is displayed in another area of the screen. The user may view the different images on the screen for diagnosis. The additional information helps the user diagnose the region.

Figure 6:
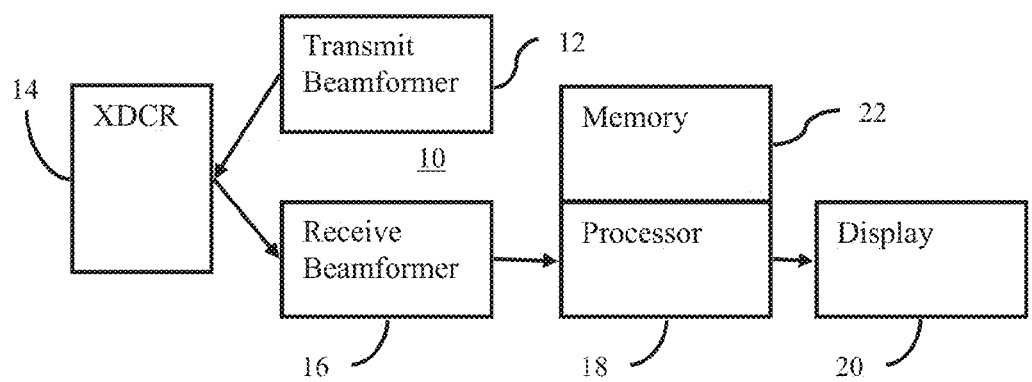
FIG. 6 is a block diagram of one embodiment of a system for shear wave estimation from analytic data.

FIG. 6 shows one embodiment of a system 10 for shear wave estimation from analytic data. The system 10 implements the method of FIG. 1, the method of FIG. 2, or other methods. The system 10 includes a transmit beamformer 12, a transducer 14, a receive beamformer 16, an image processor 18, a display 20, and a memory 22. Additional, different or fewer components may be provided. For example, a user input is provided for user interaction with the system.

The system 10 is a medical diagnostic ultrasound imaging system. In alternative embodiments, the system 10 is a personal computer, workstation, PACS station, or other arrangement at a same location or distributed over a network for real-time or post acquisition imaging.

The transmit beamformer 12 is an ultrasound transmitter, memory, pulser, analog circuit, digital circuit, or combinations thereof. The transmit beamformer 12 is operable to generate waveforms for a plurality of channels with different or relative amplitudes, delays, and/or phasing. Upon transmission of acoustic waves from the transducer 14 in response to the generated electrical waveforms, one or more beams are formed. A sequence of transmit beams are generated to scan a two or three-dimensional region. Sector, Vector®, linear, or other scan formats may be used. The same region is scanned multiple times. For flow or Doppler imaging and for shear imaging, a sequence of scans along the same line or lines is used. In Doppler imaging, the sequence may include multiple beams along a same scan line before scanning an adjacent scan line. For shear imaging, scan or frame interleaving may be used (i.e., scan the entire region before scanning again). Line or group of line interleaving may be used. In alternative embodiments, the transmit beamformer 12 generates a plane wave or diverging wave for more rapid scanning.

The same transmit beamformer 12 generates impulse excitations or electrical waveforms for generating acoustic energy to cause displacement. Electrical waveforms for acoustic radiation force impulses are generated. In alternative embodiments, a different transmit beamformer is provided for generating the impulse excitation. The transmit beamformer 12 causes the transducer 14 to generate pushing pulses or acoustic radiation force impulse pulses.

The transducer 14 is an array for generating acoustic energy from electrical waveforms. For an array, relative delays focus the acoustic energy. A given transmit event corresponds to transmission of acoustic energy by different elements at a substantially same time given the delays. The transmit event provides a pulse of ultrasound energy for displacing the tissue. The pulse is an impulse excitation or tracking pulse. Impulse excitation includes waveforms with many cycles (e.g., 500 cycles) but that occurs in a relatively short time to cause tissue displacement over a longer time. A tracking pulse may be B-mode transmission, such as using 1-5 cycles. The tracking pulses are used to scan a region of a patient.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. Receive signals are generated in response to ultrasound energy (echoes) impinging on the elements of the transducer 14. The elements connect with channels of the transmit and receive beamformers 12, 16. Alternatively, a single element with a mechanical focus is used.

The receive beamformer 16 includes a plurality of channels with amplifiers, delays, and/or phase rotators, and one or more summers. Each channel connects with one or more transducer elements. The receive beamformer 16 is configured by hardware or software to apply relative delays, phases, and/or apodization to form one or more receive beams in response to each imaging or tracking transmission. Receive operation may not occur for echoes from the impulse excitation used to displace tissue. The receive beamformer 16 outputs data representing spatial locations using the receive signals. Relative delays and/or phasing and summation of signals from different elements provide beamformation. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental or other band.

In coordination with the transmit beamformer 12, the receive beamformer 16 generates data representing the region at different times. After the acoustic impulse excitation, the receive beamformer 16 generates beams representing locations along a plurality of lines at different times. By scanning the region of interest with ultrasound, data (e.g., beamformed samples) is generated. By repeating the scanning, ultrasound data representing the region at different times after the impulse excitation is acquired.

The receive beamformer 16 outputs beam summed data representing spatial locations. Data for a single location, locations along a line, locations for an area, or locations for a volume are output. Dynamic focusing may be provided. The data may be for different purposes. For example, different scans are performed for B-mode or tissue data than for displacement. Alternatively, the B-mode data is also used to determine displacement. As another example, data for shear imaging are acquired with a series of shared scans, and B-mode or Doppler scanning is performed separately or using some of the same data.

The processor 18 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, combinations thereof or other now known or later developed device for detecting and processing information for display from beamformed ultrasound samples. In one embodiment, the processor 18 includes one or more detectors and a separate processor. The separate processor is a control processor, general processor, digital signal processor, application specific integrated circuit, field programmable gate array, network, server, group of processors, data path, combinations thereof or other now known or later developed device for determining displacement, computing analytic displacement data, determining phase of analytic displacement data, locating a zero-crossing of the phase, identifying magnitude of displacement, calculating travel time, calculating shear wave velocity, center frequency, attenuation, shear modulus, shear viscosity, or one or more other properties of shear wave propagation, and/or generating an image. For example, the separate processor is configured by hardware and/or software to perform any combination of one or more of the acts shown in FIG. 1 or 2.

The processor 18 is configured to estimate tissue displacement induced by the acoustic impulse excitation. Using correlation, tracking, motion detection, or other displacement measuring, the amount of shift in position of the tissue is estimated. The estimation is performed multiple times through a period, such as from prior to the tissue moving due to the impulse to after the tissue has mostly or completely returned to a relaxed state (e.g., recovered from the stress caused by the impulse excitation).

The processor 18 is configured to compute analytic displacement data. The displacements over time for one or more locations are converted into a complex representation. For example, the Hilbert transform is applied to the displacement data for a location. The magnitude and phase may be determined from the complex representation.

The processor 18 is configured to determine a zero-crossing of the phase for each of various locations. The slope of the phase for one or more locations may be calculated. The peak magnitude may be found. Differences in time and distance may be used to calculate velocity. Attenuation and/or dispersion of the shear wave may be calculated from the analytic displacement data. Shear modulus, shear viscosity, velocity, center frequency or other characteristic of the shear wave are estimated by the processor 18.

The processor 18 implements a filter. Any filter, such as a finite or infinite impulse response filter, is created. The pass band of the filter is programmable so that the same analytic displacement data may be filtered with different pass bands and corresponding center frequencies. The dispersion of the shear wave is calculated using the filtering. In alternative embodiment, one or more filters separate from the processor 18 are used. The filtered analytic displacement data or filtered magnitude and/or phase may be used for estimating characteristics of the shear wave.

The processor 18 is configured to generate one or more images. For example, a shear wave velocity image is generated. The shear wave velocity image is presented as an overlay or region of interest within a B-mode image. The shear wave velocity modulates the color at locations in the region of interest. Where the shear wave velocity is below a threshold, B-mode information may be displayed without modulation by the shear wave velocity.

Other information is included in the image, displayed sequentially or substantially simultaneously, or used instead. For example, a shear modulus, shear viscosity, or center frequency image is displayed at a same time as the shear wave velocity. Each is generated as a color overlay in the region of interest in B-mode images. The velocity and other shear characteristic may be combined as a single overlay on one B-mode image. Alternatively, the other characteristic is displayed as text or a numerical value adjacent or overlaid on a B-mode or shear wave velocity imaging image. The processor 18 may be configured to generate other displays. For example, the shear wave velocity image is displayed next to a graph, text, or graphical indicators of another shear wave characteristic. The information in addition to the shear wave velocity is presented for one or more locations of the region of interest without being in a separate two or three-dimensional representation.

The processor 18 operates pursuant to instructions stored in the memory 22 or another memory for shear wave estimation from analytic data. The memory 22 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 20 is a CRT, LCD, projector, plasma, or other display for displaying two-dimensional images or three-dimensional representations. The two dimensional images represent spatial distribution in an area. The three-dimensional representations are rendered from data representing spatial distribution in a volume. The display 20 is configured by the processor 18 or other device by input of the signals to be displayed as an image. The display 20 displays an image representing shear for different locations in a region of interest or an entire image.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for shear wave estimation from analytic data, the method comprising:

transmitting an acoustic radiation force excitation into a patient;

measuring, with ultrasound, displacements at locations of tissue within the patient in response to a shear wave resulting from the acoustic radiation force excitation;

constructing, by a processor, analytic data in a time domain from the measured displacements, the analytic data comprising a complex representation constructed from the measured displacements as a real representation;

estimating a characteristic of the shear wave from the analytic data wherein estimating the characteristic comprises computing magnitudes with or without phases from the analytic data and estimating a group velocity from peak magnitudes of the computed magnitudes of the analytic data for the measured displacements from at least two locations; and displaying an image that is a function of the characteristic.

2. A method for shear wave estimation from analytic data, the method comprising:

transmitting an acoustic radiation force excitation into a patient;

measuring, with ultrasound, displacements at locations of tissue within the patient in response to a shear wave resulting from the acoustic radiation force excitation;

constructing, by a processor, analytic data in a time domain from the measured displacements, the analytic data comprising a complex representation constructed from the measured displacements as a real representation;

estimating a characteristic of the shear wave from the analytic data wherein estimating the characteristic comprises computing phases from the analytic data and estimating a center frequency from a slope of the phases as a function of time; and displaying an image that is a function of the characteristic.

3. A method for shear wave estimation from analytic data, the method comprising:

transmitting an acoustic radiation force excitation into a patient;

measuring, with ultrasound, displacements at locations of tissue within the patient in response to a shear wave resulting from the acoustic radiation force excitation;

constructing, by a processor, analytic data in a time domain from the measured displacements, the analytic data comprising a complex representation constructed from the measured displacements as a real representation;

estimating a characteristic of the shear wave from the analytic data wherein estimating the characteristic comprises computing phases from the analytic data, determining velocity as a function of frequency, and estimating shear modulus, viscosity, or shear modulus and viscosity as a function of the velocity; and displaying an image that is a function of the characteristic.

4. A method for shear wave estimation from analytic data, the method comprising:

transmitting an acoustic radiation force excitation into a patient;

measuring, with ultrasound, displacements at locations of tissue within the patient in response to a shear wave resulting from the acoustic radiation force excitation;

constructing, by a processor, analytic data in a time domain from the measured displacements, the analytic data comprising a complex representation constructed from the measured displacements as a real representation;

estimating a characteristic of the shear wave from the analytic data wherein estimating the characteristic comprises computing a maximum of the measured displacements over time for each of the locations, calculating a slope of the maximums of the measured displacements over the locations, and estimating attenuation of the shear wave from the slope; and displaying an image that is a function of the characteristic.

5. A method for shear wave estimation from analytic data, the method comprising:

transmitting an acoustic radiation force excitation into a patient;

measuring, with ultrasound, displacements at locations of tissue within the patient in response to a shear wave resulting from the acoustic radiation force excitation;

constructing, by a processor, analytic data in a time domain from the measured displacements, the analytic data comprising a complex representation constructed from the measured displacements as a real representation;

estimating a characteristic of the shear wave from the analytic data wherein estimating comprises computing phase and magnitude of the analytic data for the locations, finding zero-crossings of the phases of the locations by monotonic function fitting, and estimating group velocity from the zero-crossings; and displaying an image that is a function of the characteristic.

6. A method for shear wave estimation from analytic data, the method comprising:

transmitting an acoustic radiation force excitation into a patient;

measuring, with ultrasound, displacements at locations of tissue within the patient in response to a shear wave resulting from the acoustic radiation force excitation;

constructing, by a processor, analytic data in a time domain from the measured displacements, the analytic data comprising a complex representation constructed from the measured displacements as a real representation;

estimating a characteristic of the shear wave from the analytic data;

wherein estimating comprises filtering the analytic data for each location with a plurality of filters having different pass bands, calculating velocity for each of the pass bands, and estimating shear modulus and viscosity from the velocity as a function of frequencies of the pass bands and displaying an image that is a function of the characteristic.

7. A non-transitory computer readable storage medium having stored therein data representing instructions executable by a programmed processor for shear wave estimation from analytic data, the storage medium comprising instructions for:

measuring, with ultrasound, real displacement data at locations of tissue within a patient in response to a shear wave resulting from an acoustic radiation force excitation;

constructing analytic displacement data from the real displacement data, the analytic data comprising a complex representation of displacements of the real displacement data;

computing phases of the analytic displacement data for each of the locations;

estimating a shear wave velocity from zero crossings of the phases; and generating an image indicating the shear wave velocity.

8. The non-transitory computer readable storage medium of claim 7 wherein constructing comprises performing a Hilbert transform on the real displacement data as a function of time for each of the locations, and wherein computing the phases comprises computing phase as a function of time for each of the locations.

9. The non-transitory computer readable storage medium of claim 7 wherein estimating comprises determining a time of the zero crossing for each of the locations, and estimating the shear wave velocity as a function of a difference in the times of the zero crossings and a distance between the locations.

10. The non-transitory computer readable storage medium of claim 7 wherein estimating comprises determining the zero crossings from a fit of the phase to a monotonic function.

11. The non-transitory computer readable storage medium of claim 7 further comprising calculating a center frequency of a shear wave as a function of a slope of the phases as a function of time.

12. A non-transitory computer readable storage medium having stored therein data representing instructions executable by a programmed processor for shear wave estimation from analytic data, the storage medium comprising instructions for:
  measuring, with ultrasound, real displacement data at locations of tissue within a patient in response to a shear wave resulting from an acoustic radiation force excitation;
  constructing analytic displacement data from the real displacement data, the analytic displacement data comprising a complex representation of displacements of the real displacement data;
  filtering the analytic displacement data at different frequencies;
  calculating shear velocities as a function of the frequencies; and
  estimating shear modulus, viscosity, or shear modulus and viscosity from the shear velocities as a function of the frequencies.

13. The non-transitory computer readable storage medium of claim 12 wherein constructing comprises performing a Hilbert transform on the real displacement data as a function of time for each of the locations.

14. The non-transitory computer readable storage medium of claim 12 wherein filtering comprises filtering with a plurality of band pass filters having different center frequencies, wherein calculating the shear velocities comprises calculating as a function of zero-crossings of phases for each of the locations and center frequencies, and wherein estimating comprises performing a parametric curve fitting.

* * * * *